United States Patent
Moriya et al.

(10) Patent No.: US 7,560,083 B2
(45) Date of Patent: Jul. 14, 2009

(54) METHOD FOR REMOVING WATER MOLECULES FROM VACUUM CHAMBER, PROGRAM FOR EXECUTING THE METHOD, AND STORAGE MEDIUM STORING THE PROGRAM

(75) Inventors: Tsuyoshi Moriya, Nirasaki (JP); Hiroyuki Nakayama, Nirasaki (JP); Hiroshi Nagaike, Nirasaki (JP)

(73) Assignee: Tokyo Electron Limited, Tokyo (JP)

( * ) Notice: Subject to any disclaimer, the term of this patent is extended or adjusted under 35 U.S.C. 154(b) by 595 days.

(21) Appl. No.: 11/376,162

(22) Filed: Mar. 16, 2006

(65) Prior Publication Data
US 2006/0210469 A1 Sep. 21, 2006

Related U.S. Application Data

(60) Provisional application No. 60/666,717, filed on Mar. 31, 2005.

(30) Foreign Application Priority Data

Mar. 18, 2005 (JP) ............................ 2005-079165

(51) Int. Cl.
*C01B 7/01* (2006.01)
*C01B 3/02* (2006.01)
*C01B 7/19* (2006.01)
*H01L 21/3065* (2006.01)

(52) U.S. Cl. .................. 423/210; 423/248; 423/488; 423/481; 423/483; 423/655

(58) Field of Classification Search .............. 423/210, 423/248, 488, 481, 483, 655
See application file for complete search history.

(56) References Cited

U.S. PATENT DOCUMENTS

| 3,594,580 | A | * | 7/1971 | Westerlund | 252/372 |
| 4,029,754 | A | * | 6/1977 | Sata et al. | 423/579 |
| 4,519,986 | A | * | 5/1985 | Pastor et al. | 423/19 |
| 2007/0098624 | A1 | * | 5/2007 | Luly et al. | 423/483 |

OTHER PUBLICATIONS

Cicerone, R.J. "Atmospheric Carbon Tetrafluoride: A nearly Inert Gas", Sciene, New series, vol. 206, No. 4414 (Oct. 5, 1979), pp. 59-61.*
MacAndrew, J. J. et al "Using diode laser spectroscopy to evaluate techniques for acceration of etach chamber evacuation", J. Vac. Sci. Technol. A 14(3), May/Jun. 1996, pp. 1266-1272.*
Berry, R. J. et al "A computational study of the reactions of atomic hydrogen with fluoromethanes: Kinetics and product channels", Chemical Physics Letters 269 (1997), pp. 107-116.*

* cited by examiner

*Primary Examiner*—Ngoc-Yen M Nguyen
(74) *Attorney, Agent, or Firm*—Oblon, Spivak, McClelland, Maier & Neustadt, P.C.

(57) ABSTRACT

A method for removing water molecules from a vacuum chamber for carrying out a process on a target object in vacuum includes the steps of introducing into the vacuum chamber a water molecule removal gas including at least a reduction gas which reduces the water molecules to produce hydrogen molecules and a halogen-based gas which reacts with the produced hydrogen molecules to produce acid, exhausting gases in the vacuum chamber measuring an amount of water molecules present inside the vacuum chamber, and determining whether or not the measured amount of water molecules is greater than or equal to a threshold value, wherein if the measured amount of water molecules is greater than or equal to the threshold value, the water molecule removal gas is introduced into the vacuum chamber in the introducing step.

12 Claims, 5 Drawing Sheets

METHOD FOR REMOVING WATER MOLECULES FROM VACUUM CHAMBER, PROGRAM FOR EXECUTING THE METHOD, AND STORAGE MEDIUM STORING THE PROGRAM

CROSS-REFERENCE TO RELATED APPLICATIONS

This document claims priority to Japanese Patent Application Number 2005-79165, filed Mar. 18, 2005 and U.S. Provisional Application No. 60/666,717, filed Mar. 31, 2005, the entire content of which are hereby incorporated by reference.

FIELD OF THE INVENTION

The present invention relates to a method for removing water molecules from a vacuum chamber, a program for executing the method, and a storage medium storing the program.

BACKGROUND OF THE INVENTION

Conventionally, a plasma processing is carried out on a wafer serving as a substrate in a vacuum chamber, an inner wall thereof being coated with sprayed ceramic such as yttrium oxide ($Y_2O_3$) (yttria) and aluminum oxide ($Al_2O_3$). In General, since ceramic has a high reactivity with water molecules or moisture in the air, when the chamber is opened to the atmosphere by opening its lid during a regular examination or wet cleaning thereof, the water molecules may get attached to, for example, the inner wall of the chamber or an upper electrode therein.

FIG. 5 is a graph showing measurement results of an atmosphere in a plasma etching chamber (etcher) for performing a plasma etching process on the wafer, obtained by a quadropole mass spectrometer (QMS), wherein a vertical axis represents the QMS count and a horizontal axis represents the mass number.

The measurement is made right after closing the lid of the plasma etching chamber which has been opened to the atmosphere. Further, the plasma etching chamber is made of aluminum, and its inner wall is coated with alumite.

FIG. 5 shows that a peak due to molecules having a mass number of 18, which is the mass number of water molecules, is the highest, and it can be deduced therefrom that there are a large amount of water molecules present in the plasma etching chamber right after the lid has been closed. The large amount of water molecules may cause the following problems:

1) To create a vacuum inside the chamber, the inside thereof must be exhausted, and the presence of the water molecules therein increases the time required to reach the required vacuum and reduces an efficiency of a processing apparatus;

2) During a metal film forming on a wafer in a chamber of a CVD apparatus, the presence of water molecules inside the chamber may cause a number of abnormalities such as forming of an oxide film, peeling of film layers from the wafer surface and increasing of wafer surface resistance;

3) In etching of the oxide film, an etching rate of a wafer lot right after the chamber's lid is closed is different from that of the wafer lot in the chamber whose inside has become stable after a specified time period;

4) When the wafer is etched by using plasma generated by a plasma generation gas containing fluorine, water molecules in the chamber react with the plasma generation gas to form fluoric acid, the fluoric acid, in turn, corroding the inner wall surface, generating peeled particles.

5) An abnormal discharge occurring due to the presence of water molecules inside the chamber may damage the wafer and facilitate a generation of the peeled particles.

To solve the above-mentioned problems, there is known a technology wherein HCl, $BCl_3$, DCP (dichloropropane) and DMP (dimethylpropane) are introduced into the chamber (etcher) whose inner wall is coated with alumite to accelerate the removal of water molecules in the chamber (see, e.g., Journal of Vacuum Science and Technology, A14, 1266 (1996)).

In the technology, however, HCl, $BCl_3$, DCP and DMP do not readily react with water molecules. Thus, all of the water molecules emitted in form of an out gas from pores in the alumite cannot be processed, and as a result, although HCl, $BCl_3$, DCP and DMP are introduced in the chamber, it is difficult to accelerate the removal of water molecules in the chamber (etcher).

SUMMARY OF THE INVENTION

It is, therefore, an object of the present invention to provide a method for removing water molecules from a vacuum chamber, a program for executing the method, and a storage medium storing the program capable of accelerating the removal of water molecules in the chamber.

To achieve the object, in accordance with a first aspect of the present invention, there is provided a method for removing water molecules from a vacuum chamber for carrying out a process on a target object in vacuum, the method including the steps of introducing into the vacuum chamber a water molecule removal gas including at least a reduction gas which reduces the water molecules to produce hydrogen molecules and a halogen-based gas which reacts with the produced hydrogen molecules to produce acid; and exhausting gases in the vacuum chamber.

Further, in accordance with a second aspect of the present invention, there is provided a program executable on a computer for performing a method for removing water molecules from a vacuum chamber for carrying out a process on a target object in vacuum, including an introduction module for introducing into the vacuum chamber a water molecule removal gas including at least a reduction gas which reduces the water molecules to produce hydrogen molecules and a halogen-based gas which reacts with the produced hydrogen molecules to produce acid; and an exhaust module for exhausting gases in the vacuum chamber.

Further, in accordance with a third aspect of the present invention, there is provided a computer readable storage medium for storing therein a program executable on a computer for performing a method for removing water molecules from a vacuum chamber for carrying out a specified process on a target object in vacuum, wherein the program includes an introduction module for introducing into the vacuum chamber a water molecule removal gas including at least a reduction gas which reduces the water molecules to produce hydrogen molecules and a halogen-based gas which reacts with the produced hydrogen molecules to produce acid; and an exhaust module for exhausting gases in the vacuum chamber.

Accordingly, the reduction of water molecules is accelerated in the vacuum chamber and, further, the reduced water molecules can be exhausted as acid, accelerating the removal of water molecules in the vacuum chamber.

In the method for removing the water molecules from the vacuum chamber, the reduction gas may be carbon monoxide and the halogen-based gas may be carbon fluoride. Accordingly, the reduction of water molecules is further accelerated in the vacuum chamber, thereby allowing an efficient removal of water molecules from the vacuum chamber. Therefore, the removal of water molecules in the chamber can be accelerated.

In the method for removing the water molecules from the vacuum chamber, the reduction gas may be carbon monoxide and the halogen-based gas may be chlorine. Accordingly, the reduction of water molecules is further accelerated in the vacuum chamber, thereby efficiently removing water molecules from the vacuum chamber. Therefore, the removal of water molecules in the chamber can be accelerated.

The method for removing the water molecules from the vacuum chamber further includes the steps of measuring an amount of water molecules present inside the vacuum chamber; and determining whether or not the measured amount of water molecules is greater than or equal to a threshold value, wherein if the measured amount of water molecules is greater than or equal to the threshold value, the water molecule removal gas is introduced into the vacuum chamber in the introducing step. Accordingly, the water molecule removal processing in the vacuum chamber can be automatized. Thus, it is possible to reduce a downtime of an object processing apparatus including the vacuum chamber.

In the method for removing the water molecules from the vacuum chamber, the process may be an etching process carried out on the target object. Accordingly, it is possible to resolve an etching rate difference between object lots.

In the method for removing the water molecules from the vacuum chamber, the process may be a transfer process for transferring the target object. Accordingly, it is possible to prevent water molecules from being attached to the target object when it is transferred.

BRIEF DESCRIPTION OF THE DRAWINGS

The above and other objects and features of the present invention will become apparent from the following description of preferred embodiments, given in conjunction with the accompanying drawings, in which.

DETAILED DESCRIPTION OF THE PREFERRED EMBODIMENTS

A preferred embodiment of the present invention will now be described with reference to the accompanying drawings.

Figure 1:
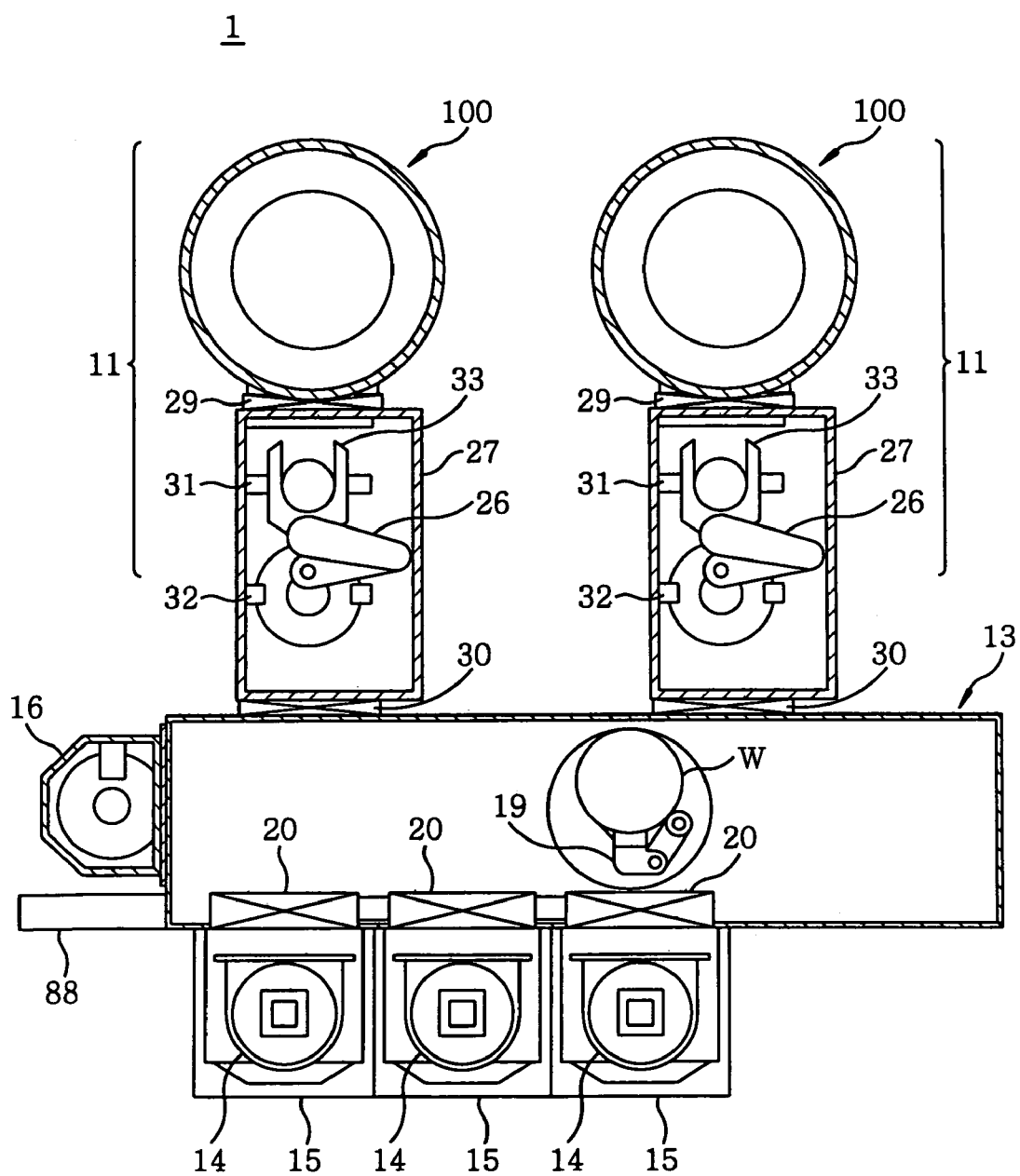
FIG. 1 is a cross sectional view showing a schematic configuration of a substrate processing apparatus including a plasma processing apparatus formed of a vacuum chamber in accordance with a preferred embodiment of the present invention.

FIG. 1 is a cross sectional view showing a schematic configuration of a substrate processing apparatus including a plasma processing apparatus formed of a vacuum chamber in accordance with the preferred embodiment of the present invention.

The substrate processing apparatus 1 shown in FIG. 1 includes two process ships 11 for carrying out a reactive ion etching (RIE) process on a wafer for semiconductor devices (hereinafter, simply referred to as a "wafer") W; and a loader module 13 that is a rectangular in shape and functions as a common transfer chamber to which the two process ships 11 are connected.

In addition to the process ships 11, connected to the loader module 13 are three FOUP mounting tables 15, each one mounting thereon a FOUP (Front Opening Unified Pod) 14 serving as a container for accommodating twenty-five wafers W; and an orienter 16 for performing a pre-alignment of the wafer W unloaded from the FOUP 14.

The two process ships 11 are connected to one of long sidewalls of the loader module 13. The three mounting tables 15 are connected to one of the other long sidewalls of the loader module 13 to face the process ships 11. The orienter 16 is coupled to one short sidewall of the loader module 13.

The loader module 13 includes a transfer arm unit 19 for transferring the wafer W disposed therein; and three wafer loading ports 20 formed at portions of the sidewall corresponding to the FOUP mounting tables 15. The wafer W is unloaded by the transfer arm unit 19 from the FOUP 14 mounted on the FOUP mounting table 15 through the loading port 20 to be loaded into the process ship 11 or the orienter 16.

The process ship 11 includes a plasma processing apparatus 100 formed of a vacuum chamber for performing an RIE process on the wafer W; and a load-lock module 27 having a transfer arm 26 for transferring the wafer W to the plasma processing apparatus 100.

The loader module 13 is maintained at an atmospheric pressure therein, whereas the plasma processing apparatus 100 of the process ship 11 is kept at a vacuum level therein. Accordingly, the load-lock module 27 is configured as a vacuum preliminary transfer chamber whose inner pressure can be controlled by a vacuum gate valve 29 and an atmospheric gate valve 30 disposed to communicate with the plasma processing apparatus 100 and the loader module 13, respectively.

A transfer arm 26 is installed in an approximately central portion of the load-lock module 27. A first buffer 31 is installed between the transfer arm 26 and the plasma processing apparatus 100 and a second buffer 32 is installed between the transfer arm 26 and the loader module 13. The first and the second buffers 31 and 32 are installed on a moving path of a wafer supporting portion 33 disposed at a leading end of the transfer arm 26. The RIE processed wafer W is temporarily moved upward from the path of the supporting portion 33 to thereby facilitate a smooth exchange of a processed wafer W with an unprocessed wafer W and vice versa in the plasma processing apparatus 100.

Further, for controlling the operations of the process ships 11, the loader module 13 and the orienter 16 (hereinafter, referred to as "each component"), the substrate processing apparatus 1 includes a system controller (not shown); and an operation controller 88 disposed at one end portion of the loader module 13.

The system controller controls an operation of each component based on a recipe, i.e., a program, corresponding to an RIE process or a wafer transfer process. The operation controller 88 includes a display unit formed of, e.g., LCD (Liquid Crystal Display), wherein the display unit presents an operation status of each component.

Figure 2:
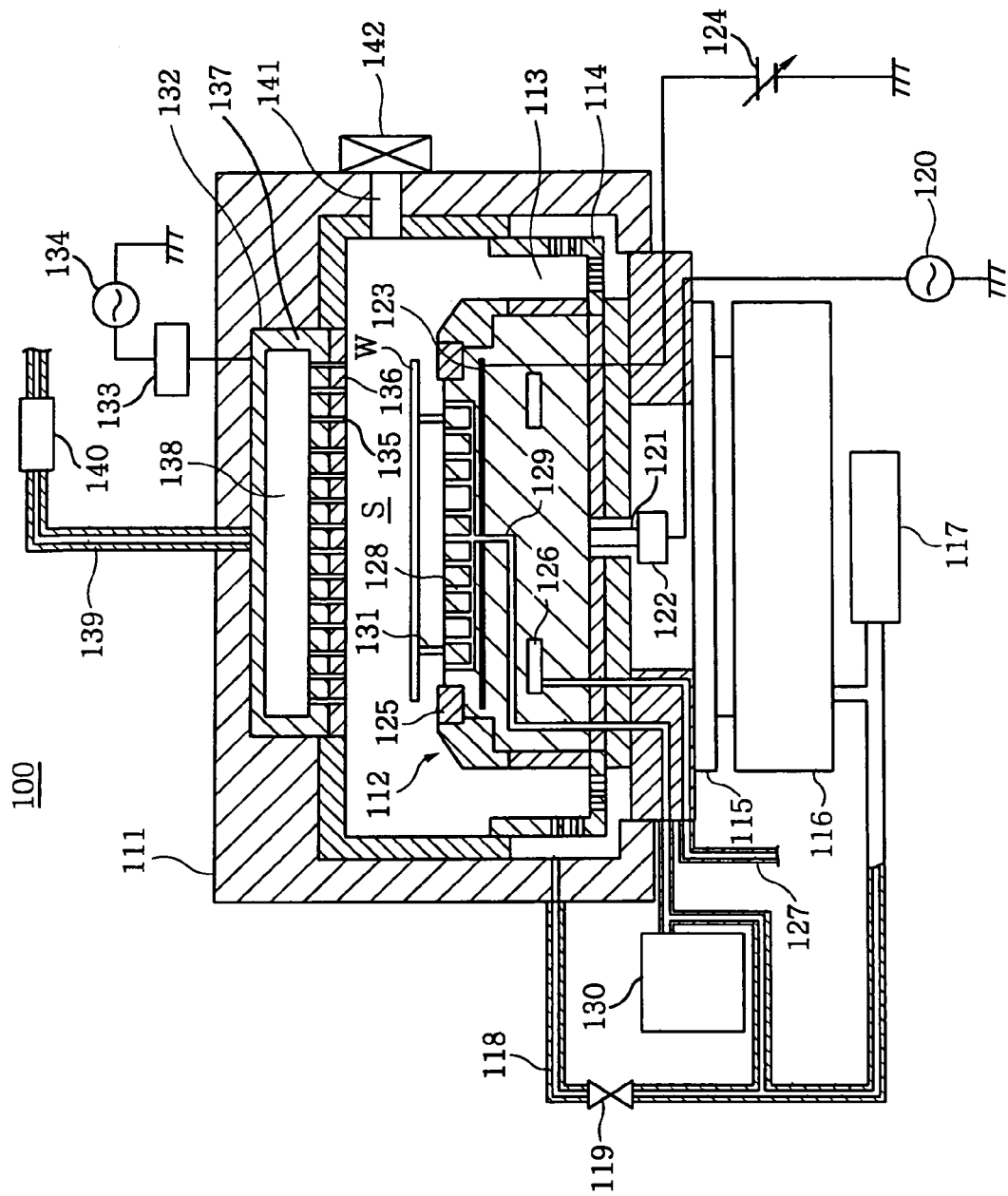
FIG. 2 is a vertical sectional view showing a schematic configuration of the plasma processing apparatus shown in FIG. 1.

FIG. 2 is a vertical sectional view showing a schematic configuration of the plasma processing apparatus shown in FIG. 1.

Referring to FIG. 2, a plasma processing apparatus 100 includes a cylindrical chamber 111 made of aluminum, having therein a cylindrical susceptor 112 employed as a mounting table for mounting thereon the wafer W of, e.g., 300 mm in diameter.

In the plasma processing apparatus 100, a gas exhaust passageway 113 serving as a flow path for discharging gas molecules from a space above the susceptor 112 to the outside is formed by an inner wall of the chamber 111 and a side surface of the susceptor 112. An annular baffle plate 114 for preventing plasma leakage is disposed in the middle of the gas exhaust passageway 113. Further, a space at the downstream side of the gas exhaust passageway 113 below the baffle plate 114 is crooked in such a way as to pass below the susceptor 112 to communicate with an automatic pressure control valve (APC) 115 that is a variable butterfly valve. The APC 115 is coupled to a turbo molecular pump (TMP) 116 employed as a gas exhaust pump for vacuum exhaust, and, further, coupled to a dry pump (DP) 117 employed as a gas exhaust pump through the TMP 116. Hereinafter, a gas exhaust channel formed of APC 115, TMP 116 and DP 117 is referred to as a "main exhaust line", which performs a pressure control in the chamber 111 by using the APC 115, and depressurizes the inside of the chamber 111 to a near-vacuum state by using the TMP 116 and the DP 117.

Further, the aforementioned space at the downstream side of the gas exhaust passageway 113 below the baffle plate 114 is also coupled to an additional gas exhaust channel (hereinafter, referred to as a "rough exhaust line"), separated from the main exhaust line. The rough exhaust line includes a gas exhaust line 118 having a diameter of, e.g., 25 mm, which communicates with the aforementioned space and the DP 117; and a valve 119 disposed in the middle of the gas exhaust line 118. By using the valve 119, the aforementioned space can be isolated from the DP 117. The rough exhaust line discharges gases from the chamber 111 by the DP 117.

A lower electrode high frequency power supply 120 is connected to the susceptor 112 through a power feed rod 121 and a matching unit 122 and supplies a predetermined high frequency power to the susceptor 112. Accordingly, the susceptor 112 serves as a lower electrode. Further, the matching unit 122 functions to maximize a supply efficiency of a high frequency power supplied to the susceptor 112 by reducing the high frequency power reflected from the susceptor 112.

At an inner upper portion of the susceptor 112, there is disposed a circular electrode plate 123 made of a conductive film. A DC power supply 124 is electrically connected to the electrode plate 123. The wafer W is adsorbed and supported on a top surface of the susceptor 112 by Columbic force or Johnsen-Rahbek force generated by a DC voltage applied from the DC power supply 124 to the electrode plate 123. Further, a circular focus ring 125 is disposed on top of the susceptor 112 to surround a periphery of the wafer W, which is adsorbed and supported on the top surface of the susceptor 112. The focus ring 125 is exposed to a space S, which will be explained later, and functions to focus ions or radicals produced in the space S onto the surface of the wafer W, thereby improving an RIE processing efficiency.

Further, an annular coolant chamber 126 extending, e.g., in the circumferential direction, is provided in the susceptor 112. A coolant, e.g., cooling water, maintained at a specified temperature is supplied to be circulated in the coolant chamber 126 from a chiller unit (not shown) through a coolant piping 127. Therefore, a processing temperature of the wafer W, which is adsorbed and supported on the top surface of the susceptor 112, is controlled by the temperature of the coolant.

At a part on the top surface of the susceptor 112 where the wafer W is adsorbed and supported (hereinafter, referred to as an "adsorption surface"), there are formed a plurality of heat transfer gas supply holes 128 and heat transfer gas supply grooves (not shown). The heat transfer gas supply holes 128 and the heat transfer gas supply grooves are coupled to a heat transfer gas supply unit 130 through a heat transfer gas supply line 129 disposed in the susceptor 112. The heat transfer gas supply unit 130 supplies a heat transfer gas, e.g., He gas, to a gap between the adsorption surface and a backside surface of the wafer W. Further, the heat transfer gas supply line 129 is connected to the gas exhaust line 118 and configured to vacuum-exhaust the gap between the adsorption surface and the backside surface of the wafer W by using the DP 117.

At the adsorption surface of the susceptor 112, there is disposed a plurality of pusher pins 131 serving as lift pins, which can be deliberately made to protrude above the top surface of the susceptor 112. These pusher pins 131, coupled to a motor (not shown) through a ball screw (not shown), move in up and down directions of FIG. 2 by a rotational movement of the motor, which is converted into a rectilinear movement by the ball screw. While the wafer W is adsorbed on the adsorption surface and the RIE process is carried out on the wafer W, the pusher pins 131 are lowered down into the susceptor 112. On the other hand, when the RIE processed wafer W is unloaded from the chamber 11, the pusher pins 131 are protrude from the top surface of the susceptor 112 to separate the wafer W from the susceptor 112 and lift it upward.

At a ceiling portion of the chamber 111, there is disposed a gas introduction shower head 132 to face the susceptor 112. The gas introduction shower head 132 is connected to an upper electrode high frequency power supply 134 through a matching unit 133. The upper electrode high frequency power supply 134 supplies a predetermined high frequency power to the gas introduction shower head 132, allowing the gas introduction shower head 132 to serve as an upper electrode. Further, the matching unit 133 serves similar functions as the aforementioned matching unit 122.

The gas introduction shower head 132 includes a bottom electrode plate 136 having a plurality of gas holes 135; and an electrode supporting member 137 for detachably supporting the electrode plate 136. Further, in the electrode supporting member 137, there is provided a buffer chamber 138 to which a processing gas supply unit (not shown) is connected via a processing gas inlet pipe 139. A pipe insulator 140 is disposed in the middle of the processing gas inlet pipe 139. The pipe insulator 140 is made of an insulator and serves to prevent a high frequency power supplied to the gas introduction shower head 132 from leaking out to the processing gas supply unit through the processing gas inlet pipe 139. Through the gas holes 135, the gas introduction shower head 132 supplies into the chamber 111 a processing gas fed from the processing gas inlet pipe 139 to the buffer chamber 138 and a water removal gas to be described later.

Further, a loading/unloading port 141 of the wafer W is provided in a sidewall of the chamber 111 at a position corresponding to the height of the wafer W when lifted upward from the susceptor 112 by the pusher pins 131; and a gate valve 142 for opening or closing the loading/unloading port 141 is attached thereto.

Furthermore, in order to monitor an amount of water molecules or moisture in the chamber 111, the chamber 111 is connected to a spectrometer (not shown) capable of measuring the amount, for example, a quadropole mass spectrometer, an infrared absorption/emission spectrometer and an ICP mass spectrometer.

In the chamber 111 of the plasma processing apparatus 100, as mentioned above, high frequency powers are applied to the space S between susceptor 112 and the gas introduction shower head 132 by supplying high frequency powers thereto. Hence, the processing gas, which has been supplied through the gas introduction shower head 132, is converted into a high-density plasma in the space S, and the RIE process is carried out on the wafer W using therewith.

Specifically, to carry out the RIE process on the wafer W in the plasma processing apparatus 100, first, the gate valve 142 is opened to load the wafer W serving as an object to be processed into the chamber 111, and a DC voltage is applied to the electrode plate 123 to adsorb and support the loaded wafer W on the adsorption surface of the susceptor 112. Further, the processing gases (e.g., gaseous mixture including $CF_4$ gas, $O_2$ gas and Ar gas, having a specified flow rate ratio) are supplied through the gas introduction shower head 132 into the chamber 111 at specified flow rates and flow rate ratio; and, at the same time, the inner pressure of the chamber 111 is set to be kept at a predetermined value by the APC 115 or the like. Still further, high frequency powers are applied to the space S in the chamber 111 by the susceptor 112 and the gas introduction shower head 132. Accordingly, the processing gases introduced through the gas introduction shower head 32 are converted into a plasma, generating ions or radicals in the space S, and the generated radicals or ions are focused on the surface of the wafer W by the focus ring 125 to etch the surface of the wafer W physically or chemically.

Further, a regular examination or wet cleaning is performed in the chamber 111 with its lid (not shown) opened and, then, a gaseous mixture including $CF_4$ and CO (hereinafter, referred to as a "water molecule removal gas") is introduced through the gas introduction shower head 132 into the chamber 111 with its lid closed. At this time, $CF_4$ and CO introduced into the chamber 111 react with $H_2O$ molecules existing therein introduced from the outside when the lid was opened or emitted from pores of the alumite coating on the inner wall of the chamber 111 as represented by the following equation (1):

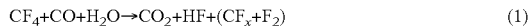

$$CF_4 + CO + H_2O \rightarrow CO_2 + HF + (CF_x + F_2) \quad (1)$$

wherein the valence is not considered.

As shown in equation (1), $CO_2$, HF, $CF_x$ and $F_2$ are produced due to a reaction between the water molecule removal gas introduced through the gas introduction shower head 132 and $H_2O$ molecules in the chamber 111. In particular, $H_2O$ molecules are reduced by CO in the water molecule removal gas to produce hydrogen molecules, and the produced hydrogen molecules react with $CF_4$ in the water molecule removal gas to produce HF. The reduction of $H_2O$ molecules is accelerated due to the presence of CO with a strong reducibility. Further, $CF_4$ is easy to be reduced and, thus, rapidly reacts with the produced hydrogen molecules, meaning that the reaction represented by equation (1) proceeds extremely rapidly. The produced $CO_2$, HF, $CF_x$ and $F_2$ are discharged to the outside from the chamber 111 by an evacuation of the TMP 116 and the DP 117.

Hereinafter, there will be described an atmosphere change in the chamber 111 caused by the reaction represented by equation (1).

Figure 3:
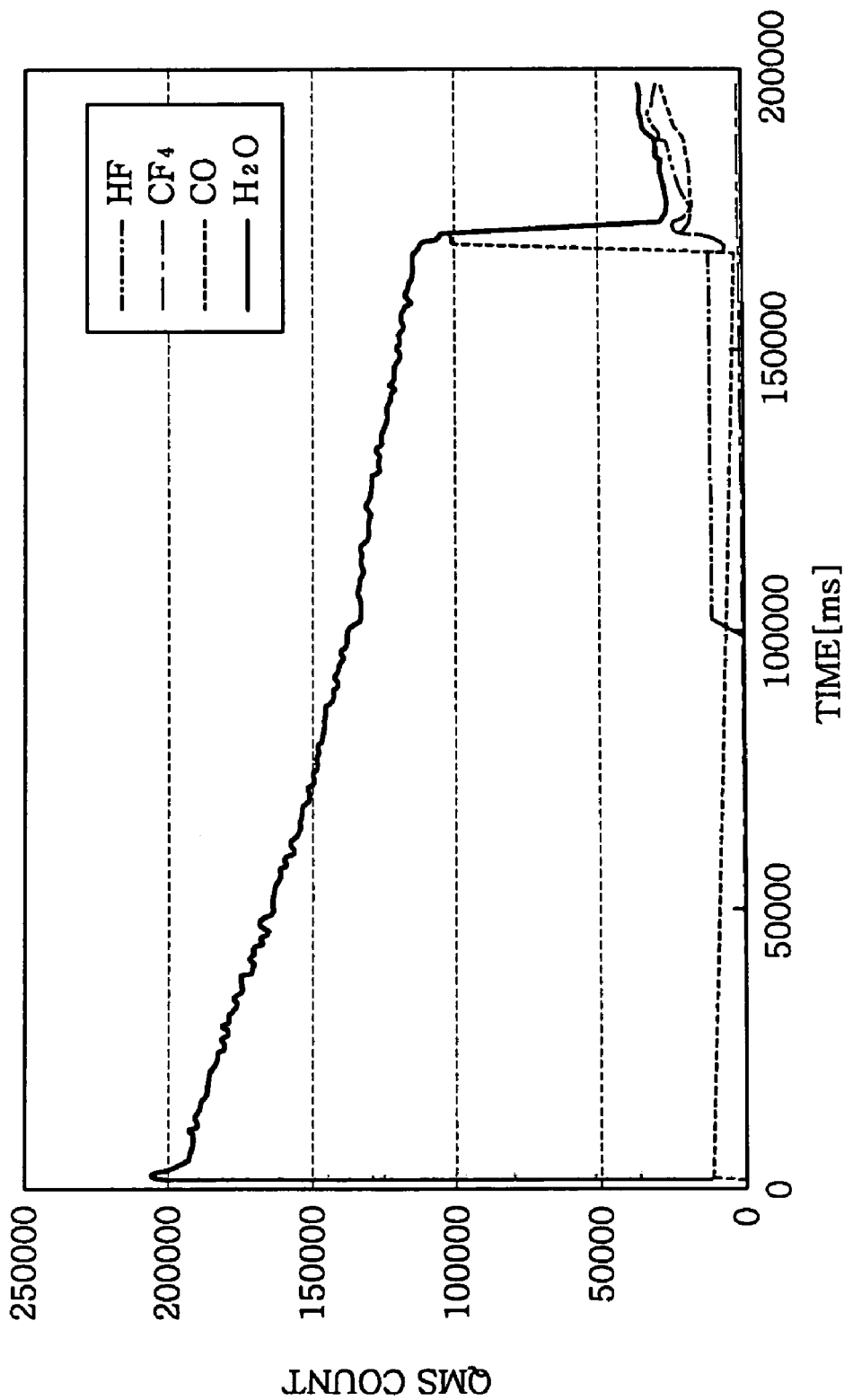
FIG. 3 is a graph showing measurement results of an atmosphere in the chamber shown in FIG. 2, which changes as a function of elapsed time and obtained by a quadropole mass spectrometer (QMS)

FIG. 3 is a graph showing measurement results of an atmosphere in the chamber shown in FIG. 2, which changes as a function of elapsed time and obtained by a quadropole mass spectrometer (QMS), wherein a vertical axis represents the QMS count and a horizontal axis, the elapsed time.

The measurements were made from the time at which the chamber 111 that had become isolated from the atmosphere when its lid was closed after having been exposed thereto when the lid thereof was opened began to be exhausted by the TMP 116 and the DP 117 until after the water molecule removal gas is introduced into the chamber 111. Further, a dashed double-dotted line represents HF; a dashed dotted line, $CF_4$; a dashed line, CO; and a solid line, $H_2O$.

From the results of FIG. 3, it can be known that the amount of $H_2O$ molecules gradually decreases as a function of the elapsed time due to the chamber being exhausted by the TMP 116 and the DP 117, and the amount of $H_2O$ molecules rapidly decreases at a time of about 170000 ms which coincides with the introduction of the water molecule removal gas, a gaseous mixture including $CF_4$ and CO. That is because the reaction represented by equation (1) extremely rapidly proceeds in the chamber 111 with the introduction of the water molecule removal gas.

As described above, by introducing the water molecule removal gas into the chamber 111 through the gas introduction shower head 132, the reduction of $H_2O$ molecules is accelerated in the chamber 111 and, further, the reduced $H_2O$ molecules are exhausted as HF, resulting in an efficient removal of $H_2O$ molecules from the inside of the chamber 111. Moreover, since $CF_4$ gas is used as a processing gas, the gas introduction shower head 132 can be also employed as a unit for introducing the water molecule removal gas. Thus, there is no need to provide new piping and the like, making it possible to suppress a cost increase of the substrate processing apparatus 1 as well as the plasma processing apparatus 100.

Figure 4:
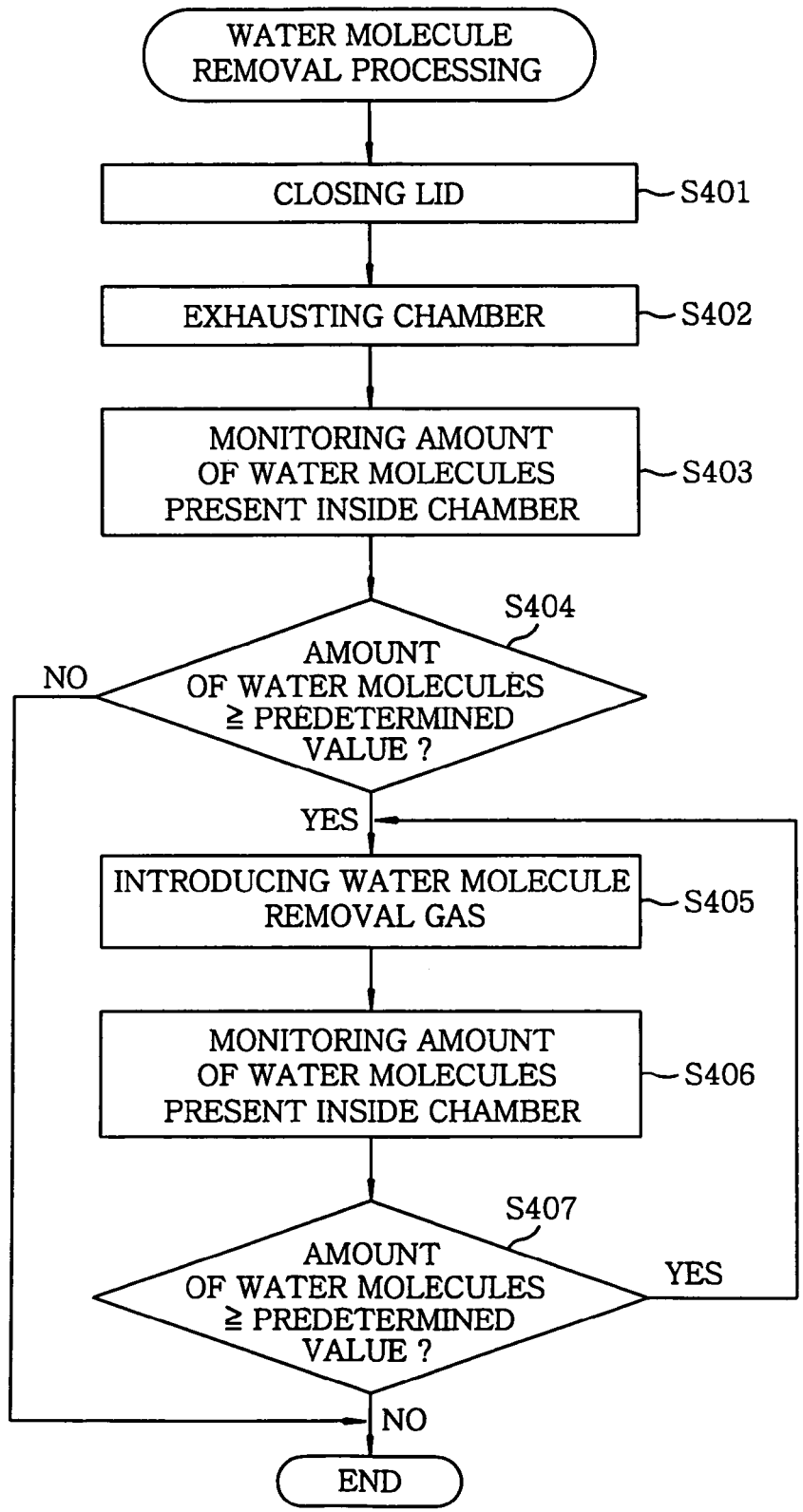
FIG. 4 is a flowchart showing a sequence of water molecule removal processing performed by a system controller in the substrate processing apparatus shown in FIG. 1.
Figure 5:
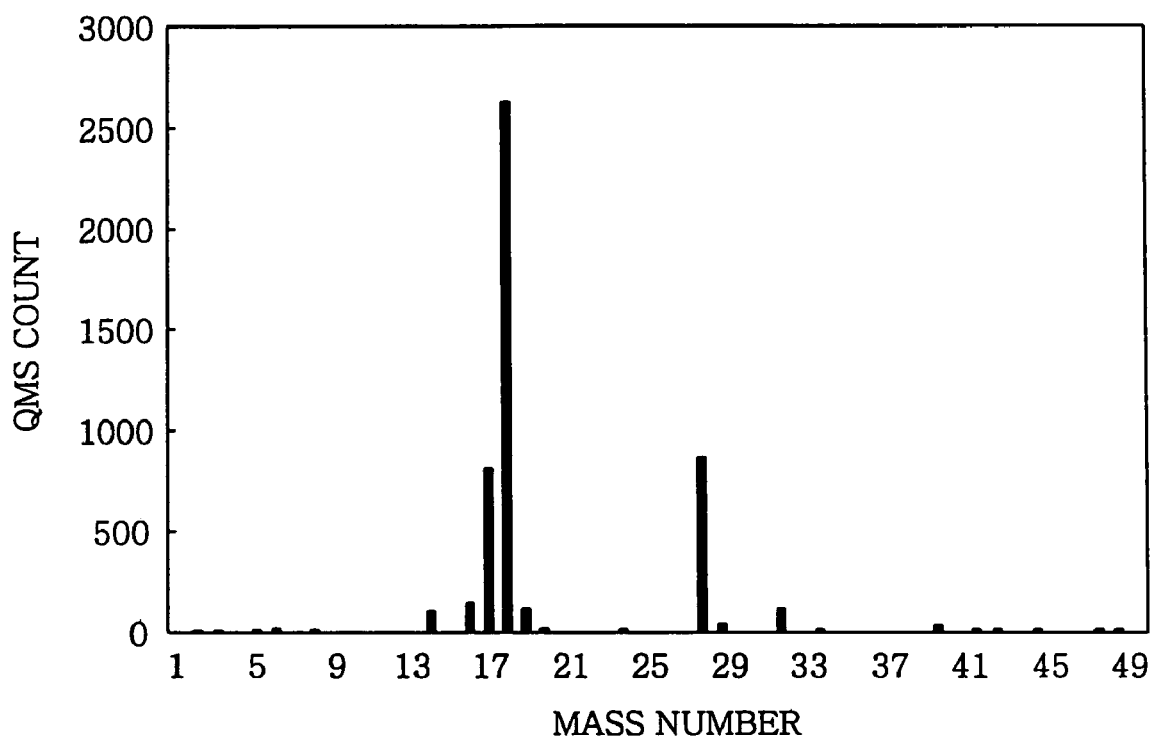
FIG. 5 is a graph showing measurement results of an atmosphere in an etcher for performing a plasma etching process on a wafer, obtained by the quadropole mass spectrometer.

FIG. 4 is a flowchart showing a sequence of water molecule removal processing performed by the system controller in the substrate processing apparatus shown in FIG. 1.

The processes shown in FIG. 4 is performed on the substrate processing apparatus that had undergone a regular examination of the plasma processing apparatus 100 or a wet cleaning of the chamber 111 during which the inside of the chamber 111 gets exposed to the atmosphere as a result of the lid being opened.

Referring to FIG. 4, the system controller controls the plasma processing apparatus 100 such that the lid of the chamber is closed (step S401); the chamber 111 is exhausted by the TMP 116 and the DP 117 (step S402); and the amount of water molecules present inside the chamber 111 is monitored by the spectrometer connected to the chamber 111 (step S403).

Subsequently, in step S404, it is determined whether or not the amount of water molecules present inside the chamber 111 is greater than or equal to a predetermined value at which the above-mentioned problems 1) to 5) occur. If the amount of water molecules present inside the chamber 111 is smaller than the predetermined value, the process is completed, whereas if the amount of water molecules present inside the chamber 111 is greater than or equal to the predetermined value, the water molecule removal gas is introduced through the gas introduction shower head 132 by controlling the processing gas supply unit (step S405).

In the next step S406, the amount of water molecules present inside the chamber 111 is monitored repeatedly to determine whether or not the amount of water molecules in the chamber 111 is greater than or equal to the predetermined value (step S407). If the amount of water molecules in the chamber 111 is monitored to be greater than or equal to the predetermined value, the process returns to the step S405. If the amount of water molecules in the chamber 111 is found to be smaller than the predetermined value, the process is stopped immediately.

Further, while the processes shown in FIG. 4 are performed, the surface of the inner wall of the chamber 111 is maintained at a high temperature. The reason thereof will be described below.

The vapor pressure of HF produced by the reaction between the water molecule removal gas and $H_2O$ molecules is 20 KPa at a temperature of $-20°$ C.; 30.9 KPa at $-10°$ C.; 47.3 KPa at $0°$ C.; 70.7 KPa at $10°$ C.; 102 KPa at $20°$ C.; and 139 KPa at $30°$ C. Accordingly, in a depressurized state where the pressure inside the chamber 111 is lower than a standard atmospheric pressure (about 101 KPa), HF is assumed to get vaporized at a temperature of about $20°$ C. or more. In other words, it is supposed that if the temperature of the inner wall surface of the chamber 111 is greater than or equal to the room temperature, the produced HF is vaporized and then discharged to the outside from the chamber 111 by the TMP 116 and the DP 117 without getting attached to the inner wall surface of the chamber 111. Therefore, by maintaining the surface of the inner wall of the chamber 111 at a high temperature, it is possible to surely prevent the produced HF from being attached to the inner wall surface of the chamber 111 and prevent the vaporized HF from being re-attached to the inner wall surface of the chamber 111, thereby preventing the inner wall surface of the chamber 111 from being corroded due to HF attached thereto.

Further, by maintaining the inner wall surface of the chamber 111 coated with a ceramic material having a plurality of pores, such as alumite, at a high temperature, $H_2O$ molecules included in the pores to become an out gas by being vaporized, accelerating the removal of water molecules.

According to the processes shown in FIG. 4, the system controller of the plasma processing apparatus 100 conducts an evacuation of the chamber 111 by using the TMP 116 and the DP 117 (step S402). When the amount of water molecules in the chamber 111 becomes greater than or equal to the predetermined value (YES at step S404), the water molecule removal gas gets introduced through the gas introduction shower head 132 (step S405), resulting in an efficient removal of $H_2O$ molecules present in the chamber 111, accelerating the removal of water molecules in the chamber 111. Further, after closing the lid of the chamber 111 which had been exposed to the atmosphere, the amount of water molecules in the chamber 111 can be automatically made to be less than the predetermined value, thus providing an environment for automatically starting the wafer processing, which is known as an auto-standby function, making it possible to reduce a downtime of the plasma processing apparatus 100 including the chamber 111.

Although, the water molecule removal gas including $CF_4$ and CO is introduced through the gas introduction shower head 132 in this embodiment, any gaseous mixture including a halogen-based processing gas (e.g., chlorine gas) and a reduction gas may be used as the water molecule removal gas without being limited thereto.

Although the water molecule removal gas is only introduced through the gas introduction shower head 132 in this embodiment, a non-reactive gas such as argon and nitrogen may be introduced together with the gaseous mixture, which, as well as providing an environmental consideration by reducing the amount of $CF_4$ or CO used, makes it possible to curtail the time from an end of the water molecule removal processing to a start of the wafer processing by generating a viscous flow, attracting HF and the like, as a consequence of the pressure in the chamber 111 being increased.

Although the inner wall surface of the chamber 111 is coated with alumite in this embodiment, the inner wall surface may be coated with $Y_2O_3$ by spraying, resulting in relatively large pores being present on the surface of the inner wall of the chamber 111. In the relatively large pores, the water molecule removal gas introduced may easily enter the pores and $H_2O$ molecules included therein may easily be vaporized to become an out gas, thereby accelerating the removal of water molecules in the chamber.

Further, instead of the sprayed $Y_2O_3$, hydration-treated $Y(OH)_3$ may be used. The hydration treatment is to form $Y(OH)_3$, a hydroxide, by reacting $Y_2O_3$ with $H_2O$. Since $Y(OH)_3$ is extremely stabilized and has a hydrophobic property, allowing it to prevent a separation of chemically adsorbed $H_2O$ and to suppress further an adsorption of $H_2O$ molecules, the inner wall surface of the chamber 111 thus sprayed becomes hydrophobic, whereby, as well as making the inner wall surface of the chamber 111 denser, $H_2O$ molecule attachment can be minimized, making it possible to reduce the generation of an out gas therefrom, further accelerating the removal of water molecules in the chamber 111.

Further, the inner wall surface of the chamber 111 may be coated with metal such as aluminum and stainless steel, quartz or the like, instead of ceramic materials such as $Al_2O_3$ and $Y_2O_3$. Since metals such as aluminum and stainless steel, quartz or the like have therein less concentration of pores, the correspondingly less amount of $H_2O$ molecules present in the chamber 111 are prevented from being attached to the inner wall surface of the chamber 111, which will further accelerate the removal of water molecules in the chamber 111.

Further, when the exhaust of the chamber 111 is performed by using the TMP 116 and the DP 117, pumping and purging, that is, gas introduction and exhaust, may be repeated. During the pumping and purging, the exhaust is performed in a state where the viscous flow is generated due to an increased pressure in the chamber 111 by the gas introduction, allowing an efficient removal of water molecules from the chamber 111.

Moreover, the chamber 111 may include a cryo pump which has a very low temperature surface, allowing the exhaust to be carried out by condensing or adsorbing gas molecules on the very low temperature surface, resulting in accelerating the removal of water molecules from the chamber 111.

Although the processes shown in FIG. 3 are carried out to remove water molecules from the chamber 111 in this embodiment, the processes may performed for the removal of water molecules in the load-lock module 27 without being limited thereto. Accordingly, it is possible to reduce a downtime of the load-lock module 27 and also prevent $H_2O$ molecules from being attached to the wafer W when the wafer W is transferred.

Although the processes shown in FIG. 3 are performed after the chamber 111 has been exposed to the atmosphere in this embodiment, the processes may be performed for each wafer lot without being limited thereto. Accordingly, the amount of water molecules in the chamber 111 can be always maintained below a fixed level, thereby resolving an etching rate difference between wafer lots.

Further, a storage medium storing therein program codes of software for realizing the functions of the aforementioned preferred embodiments is provided to the system controller. CPU or MPU included in the system controller reads the program codes stored in the storage medium and executes them, so that the object of the present invention can be achieved ultimately.

In this case, the program codes read from the storage medium execute themselves the functions of the preferred embodiments described above, meaning that the program codes and the storage medium storing therein the program codes are also part of the present invention.

Further, floppy (registered trademark) disk, hard disk, optical disk, magneto-optical disk, CD-ROM, CD-R, CD-RW, DVD-ROM, DVD-RAM, DVD-RW, DVD+RW, magnetic tape, nonvolatile memory card, ROM, etc. can be employed as the storage medium for providing the program codes. In addition, the program codes may be downloaded through the network.

Although the functions of the aforementioned preferred embodiments are realized by executing the program codes read by the CPU in the above-described case, based on instructions of the program codes, OS (operating system) operating on the CPU may execute the functions partially or entirely, and such an approach is also included in the present invention.

Further, after the program codes read from the storage medium are stored in a memory included in a function extension board inserted in the system controller or a function extension unit connected to the system controller, based on instructions of the program codes, CPU and the like included in the function extension board or the function extension unit may partially or entirely execute the functions of the above-described preferred embodiments. This approach is also part of the present invention.

While the invention has been shown and described with respect to the preferred embodiments, it will be understood by those skilled in the art that various changes and modifications may be without departing from the spirit and scope of the invention as defined in the following claims.

What is claimed is:

1. A method for removing water molecules from a vacuum chamber that performs a process on a target object in vacuum, the method comprising the steps of:
   introducing into the vacuum chamber a water molecule removal gas including a reduction gas, which reduces the water molecules to produce hydrogen molecules, and a halogen-based gas, which reacts with the produced hydrogen molecules to produce a product gas including an acid; and
   exhausting the product gas from the vacuum chamber.

2. The method of claim 1, wherein the reduction gas is carbon monoxide and the halogen-based gas is carbon fluoride.

3. The method of claim 1, wherein the reduction gas is carbon monoxide and the halogen-based gas is chlorine.

4. The method of claim 1, further comprising the steps of:
   measuring an amount of water molecules present inside the vacuum chamber; and
   determining whether or not the measured amount of water molecules is greater than or equal to a threshold value,
   wherein if the measured amount of water molecules is greater than or equal to the threshold value, the water molecule removal gas is introduced into the vacuum chamber in the introducing step.

5. The method of claim 1, wherein the process is an etching process performed on the target object.

6. The method of claim 1, wherein the process is a transfer process for transferring the target object.

7. The method of claim 2, wherein the process is an etching process performed on the target object.

8. The method of claim 2, wherein the process is a transfer process for transferring the target object.

9. The method of claim 3, wherein the process is an etching process performed on the target object.

10. The method of claim 3, wherein the process is a transfer process for transferring the target object.

11. The method of claim 4, wherein the process is an etching process performed on the target object.

12. The method of claim 4, wherein the process is a transfer process for transferring the target object.

* * * * *